US008656928B2

(12) United States Patent
Carlson et al.

(10) Patent No.: US 8,656,928 B2
(45) Date of Patent: Feb. 25, 2014

(54) ECHOGENIC MEDICAL DEVICE AND METHOD OF FORMING ECHOGENIC SURFACE

(75) Inventors: James M. Carlson, Bloomington, IN (US); Andrew Herold, Bloomington, IN (US); Ronan Young, Spencer, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1369 days.

(21) Appl. No.: 11/665,460

(22) PCT Filed: Oct. 12, 2005

(86) PCT No.: PCT/US2005/036515
§ 371 (c)(1),
(2), (4) Date: Jun. 28, 2007

(87) PCT Pub. No.: WO2006/044374
PCT Pub. Date: Apr. 27, 2006

(65) Prior Publication Data
US 2008/0097213 A1      Apr. 24, 2008

Related U.S. Application Data

(60) Provisional application No. 60/618,915, filed on Oct. 14, 2004.

(51) Int. Cl.
*A61B 8/14*          (2006.01)
(52) U.S. Cl.
USPC ........................................................ 128/897
(58) Field of Classification Search
USPC ........................................................ 600/1–8
See application file for complete search history.

(56) References Cited

U.S. PATENT DOCUMENTS

| 4,401,124 | A |   | 8/1983 | Guess et al. |
| 4,869,259 | A | * | 9/1989 | Elkins ........................... 600/458 |
| 5,081,997 | A |   | 1/1992 | Bosley, Jr. et al. |
| 5,201,314 | A | * | 4/1993 | Bosley et al. ................. 600/458 |
| 5,289,831 | A |   | 3/1994 | Bosley |
| 5,759,154 | A | * | 6/1998 | Hoyns ........................... 600/458 |
| 6,306,094 | B1 |  | 10/2001 | Joseph |
| 6,358,211 | B1 | * | 3/2002 | Mamayek ...................... 600/459 |
| 6,632,176 | B2 | * | 10/2003 | McIntire et al. .............. 600/439 |
| 6,725,083 | B1 | * | 4/2004 | Burbank et al. .............. 600/431 |
| 6,730,064 | B2 |  | 5/2004 | Ragheb et al. |
| 2003/0135117 | A1 | * | 7/2003 | Ward et al. ..................... 600/439 |
| 2006/0025852 | A1 | * | 2/2006 | Armstrong et al. ........... 623/1.17 |

OTHER PUBLICATIONS

Clark-MXR, Inc.; Machining with Long Pulses; "Micromachining Handbook"; Chapter 3, p. 1-4; obtained from the Internet on Aug. 13, 2004.

(Continued)

*Primary Examiner* — Samuel Gilbert
(74) *Attorney, Agent, or Firm* — Brinks Gilson & Lione

(57) ABSTRACT

Medical devices are made visible under ultrasonic or magnetic imaging techniques by adding a series of features on their surfaces. The features are desirably placed at more than one angle to the surface in order to enhance the visibility of the surface. Laser-machining can make a series of depressions or voids that are symmetric with respect to the surface and another series of depressions or voids that are non-symmetric. The pattern of voids is also varied by using more than one size of void, the depth of the voids, and the distribution of voids, i.e. more voids in some areas than others.

12 Claims, 3 Drawing Sheets

(56) References Cited

OTHER PUBLICATIONS

Clark-MXR, Inc.; Machining with Ultrafast Laser Pulses; "Micromachining Handbook"; Chapter 5, p. 1-3; obtained from the internet on Aug. 13, 2004.

Clark-MXR, Inc.; Stochastic or Deterministic Nature of the Ablation Process; "Micromachining Handbook"; p. 1-5; obtained from the Internet on Aug. 13, 2004.

Crosby, Paul; Get to Know Lasers and Their Roles in Plastics; "Plastics Technology-Online Article"; Jun. 2002; p. 1-4; Gardner Publications, Inc.; USA; obtained from the Internet on Aug. 16, 2004.

Niebel, Benjamin W., et al.; Use of Lasers; "Modern Manufacturing Process Engineering"; 1989; p. 539 and cover; McGraw-Hill Publishing Company; New York.

What's Your Wavelength?; http://science.howstuffworks.com/laser8.htm; p. 1; obtained from the Internet on Aug. 12, 2004.

Lasers Machine Tubes to Take on New Forms; Product news from Spectralytics; http://www.manufacturingtalk.com/news/sra/sra100.html; p. 1; obtained from the internet on Aug. 16, 2004.

UT Material Properties Table; NDT Resource Center; http://www.ndt-ed.org/EducationResources/CommunityCollege/Ultrasonics/Reference%20Inform . . . ; p. 1; obtained from the internet on Jul. 29, 2004.

Wilson-Cook: Biliary/Pancreatic E.R.C.P. Catheters; Wilson-Cook Medical GI Endoscopy; http://www.cookgroup.com/wilson_cook/biliary/ercp/ercp01.html; p. 1; obtained from the internet on Aug. 13, 2004.

Rapid Atraumatic PCNL Stone Extraction; Cook Urological—Perc NCircle; http://www.cookurological.com/features/percNcircle.html; p. 1; obtained from the internet on Aug. 13, 2004.

ERCP; Google Search; http://www.google.com/search?hl=en&ie=UTF-8&q=ERCP&btnG=Google+Search; p. 1; obtained from the internet on Aug. 13, 2004.

* cited by examiner

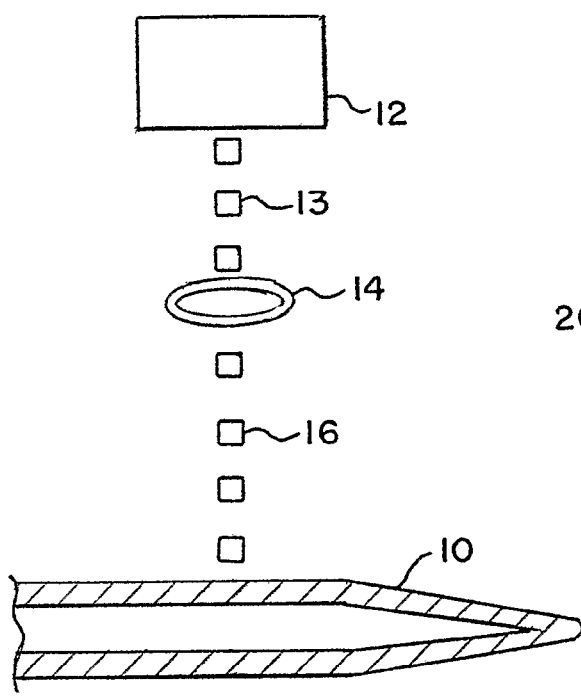
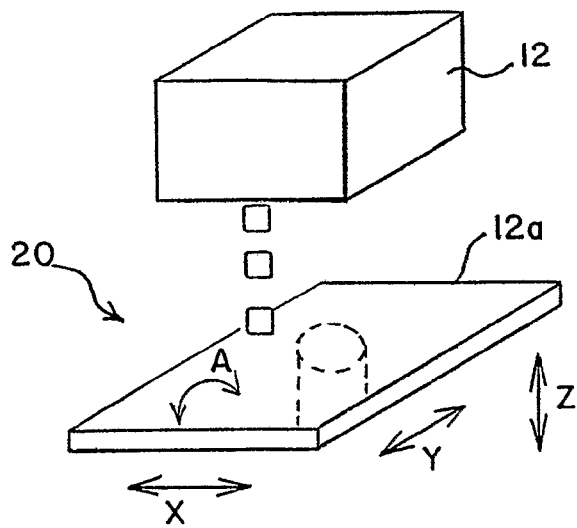
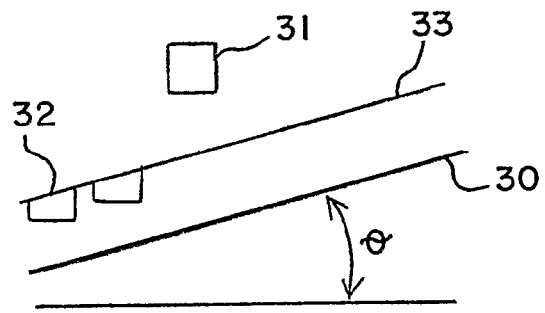
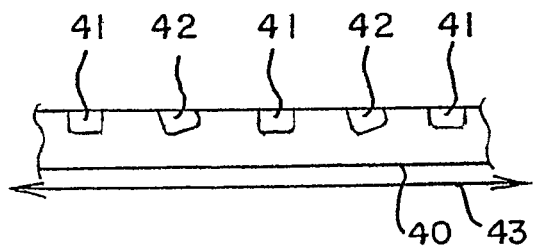

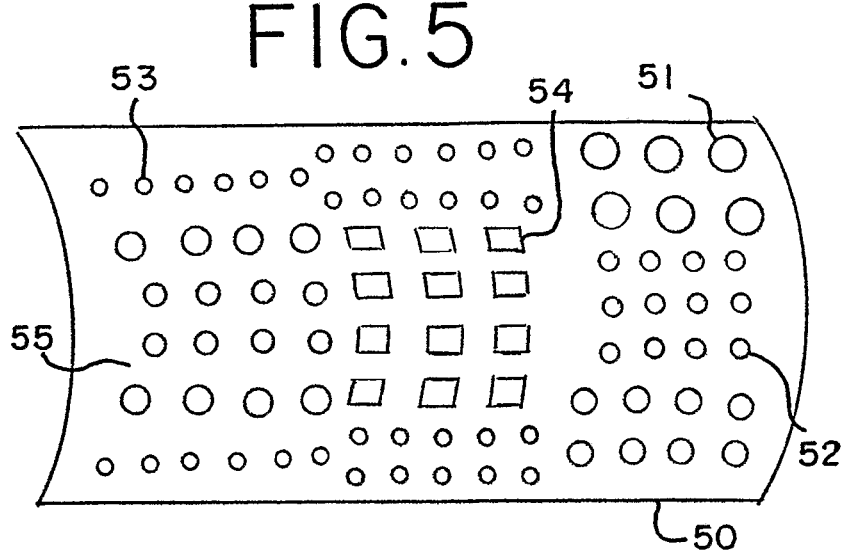
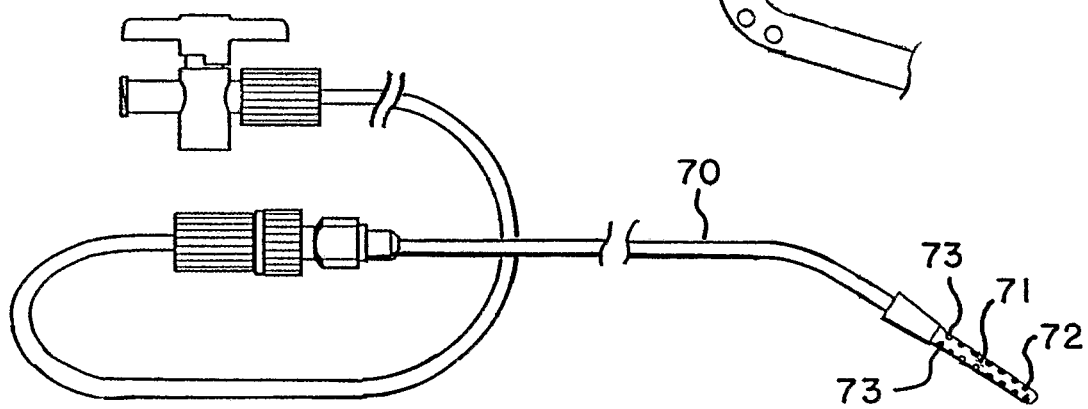
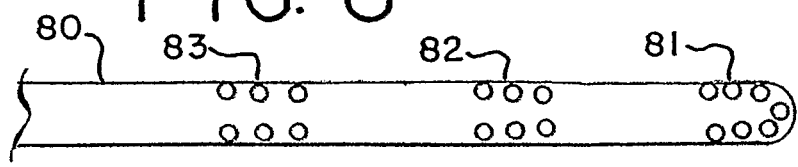

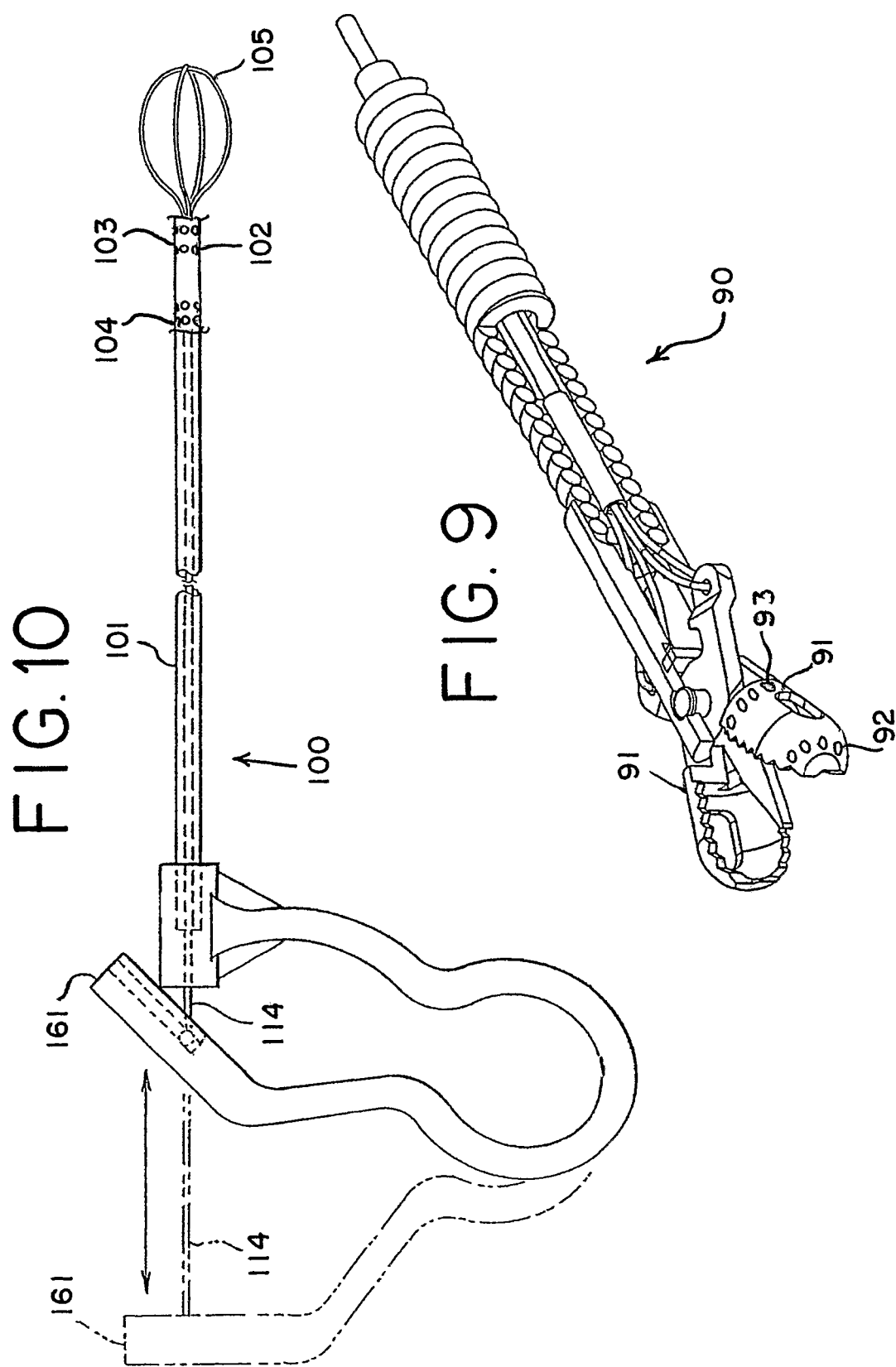

ECHOGENIC MEDICAL DEVICE AND METHOD OF FORMING ECHOGENIC SURFACE

CROSS-REFERENCE TO RELATED APPLICATIONS

The present application is the National Phase of International Application No. PCT/US05/36515, filed on Oct. 12, 2005, which claims the priority of U.S. Provisional Application No. 60/618915, filed on Oct. 14, 2004.

FIELD OF THE INVENTION

The field of the invention is that of medical devices, especially those medical devices for which visibility is desirable by ultrasound, magnetic resonance, or other imaging techniques while the device is being used inside a person's body. The field includes the formation and manufacture of such devices.

BACKGROUND

Laparoscopic or endoscopic surgery, requiring only a small opening in a patient to perform a medical procedure, is a great advance in medical science. Patients endure much less pain and suffering, because the surgeon is able to use a much smaller cut or opening, in order to perform a given procedure. These advances have occurred in almost all branches of surgery, including gynecological, urological, and vascular surgery, even extending to neurosurgery. The surgeon is able to perform these procedures by remotely manipulating a great many instruments. Of course, the surgeon must be able to see what he or she is doing, so that he or she is able to control the instruments and to correctly and efficiently perform the procedure in question.

Medical imaging techniques have thus struggled to keep pace with the advances in surgery, especially the minimally-invasive techniques that allow these procedures. Thus, a large variety of endoscopes, ureteroscopes, ultrasound machines, and fluoroscopes, along with ultrasound machines, magnetic resonance (MR) imagers, and the like, have arisen and are being used by surgeons and medical professionals to guide their accomplishment of such procedures. Those skilled in the medical arts have especially welcomed ultrasound imaging techniques, which are enhanced through the use of echogenic devices. Echogenic devices are devices whose surface has been "dimpled" or roughened in a particular manner to enhance their detection by ultrasound equipment.

Echogenic surfaces, as described in U.S. Pat. Nos. 5,981,997 and 5,201,314, are typically hemispherical or curved, allowing distortion of the sound wave as it reflects from the surface. This interference is then detected by the ultrasound machine, and the pattern of interference is interpreted as an image. In this manner, catheters, needles, and a great variety of objects may be inserted into a human or animal body, and their presence and location detected.

At least one difficulty with echogenic devices, however, is the relatively imprecise image that is available to the surgeon or other medical professional. A better way to form a medical device with a detectable or echogenic surface is needed. A medical device with an echogenic surface that may be more precisely located within a patient is also desired.

BRIEF SUMMARY

There are many embodiments of the invention. One aspect of the invention is a medical device. The medical device has an external surface with a first plurality of small surfaces on a portion of the external surface of the medical device in a first orientation relative to the medical device. The device also has a second plurality of small surfaces on the medical device in a second orientation relative to the medical device, such that the orientation of the second plurality differs from the orientation of the first plurality, and such that the first orientation is not perpendicular to the second orientation.

Another embodiment of the invention is a medical device. The medical device includes at least one external surface, a first plurality of small features on the surface, the first plurality including a second plurality of small features, wherein the first plurality includes features of at least two different sizes and wherein the second plurality is oriented to the device in a direction other than perpendicular.

Another embodiment of the invention is a method for making a medical device having an echogenic surface on at least a portion of the medical device. The method includes steps of ablating a first plurality of small surfaces on at least a portion of an external surface of the medical device in a first orientation relative to the medical device. The method also includes ablating a second plurality of small surfaces on the medical device with a laser in a second orientation relative to the medical device, such that the orientation of the second plurality differs from the orientation of the first plurality, and such that the first orientation is not perpendicular to the second orientation. The method then includes cleaning the medical device.

There are many other embodiments of the invention, a few of which are shown in the figures and description below, which is meant to be descriptive but not limiting.

BRIEF DESCRIPTION OF THE DRAWINGS

FIG. 1 is an elevational view of a catheter needle whose outer surface is being laser machined to make it echogenic;

FIG. 2 is an isometric diagram of a laser machining center with three linear axes and at least one rotary axis;

FIG. 3 is a side view of a medical device being laser machined at an angle;

FIG. 4 is a cross-sectional view of a guide wire that has been laser machined with echogenic surfaces at two angles;

FIG. 5 depicts a variety of patterns and shapes of echogenic markings useful in embodiments of the present invention;

FIG. 6 is an embodiment of tissue markers useful with the small depressions of the present inventions;

FIG. 7 depicts a cannula with laser-made markings;

FIG. 8 depicts an angioplasty catheter with echogenic markings;

FIG. 9 depicts a biopsy forceps with two bands of laser-marked depressions about the jaws for easier detection; and FIG. 10 depicts a stone extractor for percutaneous nephrolithotomy with laser-marked bands on the distal tip.

DETAILED DESCRIPTION OF THE DRAWINGS AND THE PRESENTLY PREFERRED EMBODIMENTS

It is known that adding small features, such as protuberances or depressions, enhances the visibility of the needle, or other medical devices, when used with ultrasound. Depressions or voids are added, typically by machining or punching the features into the surface. Thus, the techniques to date have used methods in which, as a practical matter, the features are added perpendicularly to the surface or to the longitudinal axis of the device. Using lasers frees the manufacturer from this limitation and enables the addition of features that may be oriented at an angle.

Higher-power lasers, such as carbon dioxide or Nd:YAG lasers are typically, but not solely, used to achieve the high power levels needed for machining on metals. It is believed that ultra-fast machining, in which the laser light is delivered in very fast pulses, less than 10 picoseconds (less than $10 \times 10^{-12}$ seconds), is preferred for machining on medical devices. Ultrafast machining, in which the pulses of laser light are delivered in very short, fast pulses, tends to avoid formation of by-products, such as slag, in the workpiece, and also to avoid formation of a large heat-affected zone in the immediate vicinity of the machined areas.

FIG. 1 is a diagrammatic view of a medical device 10, such as a catheter needle, being laser-machined by a laser device 12, delivering short pulses of laser light 13 which are focused by a lens or waveguide 14 into focused pulses 16 for delivery to the workpiece. FIG. 2 depicts a laser machining center 20 having a laser device 12 and a mounting table 12a. Laser machining center 20 preferably has linear and rotary degrees of freedom, i.e., the ability to move the workpiece in linear axes as shown, X, Y and Z, as well as at least one rotary axis, A, for tilting mounting table 12a and a workpiece mounted on the table.

With linear motion, the workpiece may be machined along its length. With rotary motion, the workpiece may be tilted or turned, so that the echogenic features may be machined completely around a periphery of the workpiece. Examples of machining centers with a laser device include a milling machine and a lathe. A milling machine typically has at least two linear axes, and may have one or more rotary axes. A lathe has at least one linear axis and a rotary axis that is very useful for machining medical devices having the general form of a cylinder. Examples include catheters, needles, and stents.

In practice, a workpiece which is desirably echogenic is mounted on a machining fixture suitable for the laser machining center. A series of light pulses is then delivered as desired, as shown in FIG. 3. Workpiece 30 is thus machined by pulses 31 of laser light, adding features 32 to surface 33. In this example, workpiece 30 is oriented at an angle θ to pulses 31. This is achieved by tilting a table on a laser mill by the same angle, or by tilting the laser source on a laser-powered lathe. In this example, features 32 are oriented at angle θ to a longitudinal axis of the workpiece. Of course, if the angle is chosen as zero, then features 32 will be added perpendicularly.

In other examples, the workpiece may be made even more visible with ultrasound by adding a series of features at more than one angle. FIG. 4 depicts a guide wire 40 whose surface has been laser machined at two different angles. Features 41 are small hemispherical cavities that are perpendicular to a longitudinal axis 43 of the wire. As seen in FIG. 4, features 41 are symmetrical. Symmetrical features 41 have been added by orienting guide wire 40 perpendicularly to the laser light as it is being machined. Features 42 are small cavities that have been machined while guide wire 40 was at an angle to the longitudinal axis. Thus, features 42 are not completely symmetrical, and may be viewed as truncated hemispheres, with one side deeper into the guide wire and the other side machined more shallowly into the surface of the guide wire.

In addition, the features may be varied in other ways. FIG. 5 depicts a cannula 50 with patterns of features that vary in several ways. There are at least five patterns 51, 52, 53, 54, 55 on the surface of the cannula. Pattern 51 includes larger holes that are also cut deeper into the surface, setting off this area of cannula 50. Pattern 52 includes smaller features that are placed more closely together and are also oriented at an angle to the surface. Pattern 53 includes smaller features that are placed at 90°, or perpendicular to the surface, and are spread further apart. Pattern 54 uses rectangular voids, rather than the more usual rounded shapes. Pattern 55 includes a series of smaller voids in another area of the cannula.

Cannula 50 may have one or more of the patterns described in FIG. 5, or other patterns, placed as desired. The features are then used in order to enhance the visibility of the cannula, or other medical device, under ultrasonic imaging. Adding these features at different angles, in different sizes, and in different shapes allows users to more readily identify the medical device, and particular portions of the medical device. A first size is different from a second size if it differs in at least one of height, depth, width, diameter or circumference. The variations in patterns may also help make the marked surface more visible under an ultrasonic or MR imaging technique. One way to add variety to the patterns is to vary the sizes or depths of the marks. Marks that vary in size by at least 25 micrometers (0.001 inches) aid in these differentiations.

These advantages may also be used in other imaging techniques. For instance, magnetic resonance imaging (MRI) may be necessary in some patients, and diagnostic or therapeutic procedures performed under MR imaging. Thus, biopsy forceps or biopsy needles, cannulae, and tissue markers should be easily visible with MR imaging. As is well known, only non-magnetic materials may be used for such devices. These materials include Nitinol, commercially pure titanium and titanium alloys, commercially pure niobium and niobium alloys, commercially pure tantalum and tantalum alloys, commercially pure platinum and platinum alloys, and commercially pure palladium and palladium alloys. By "commercially pure" is meant the metal or alloy of that designation which is available commercially with low levels of impurities. For example, "commercially pure" titanium metal has a nominal composition that includes 99.6% titanium, 0.08% carbon, 0.03% iron, 0.03% nitrogen, 0.18% oxygen, and 0.015% hydrogen.

The visibility of these devices under MR imaging is improved by adding "echogenic" features, such as those described above, even though MR imaging is distinctly different from ultrasonic imaging. Many of these materials are very difficult to process and to machine by means of conventional "chip-cutting" techniques. We have found, however, that small features may be added by laser machining techniques, thus enhancing the visibility of a number of medical devices under MR imaging.

As is well-known to those having skill in medical imaging arts, the features are preferably from about 25 to about 125 micrometers (from about 0.001 inches to about 0.005 inches) in a maximum dimension. The maximum dimension may be a diameter of a hemispherical depression, a major axis of an elliptical depression, a depth of an impression or the height of a raised surface or "bump" on a medical device of interest. It is the placement of such features that gives rise to the interference with wave patterns and allows visualization of medical devices under ultrasound or other imaging techniques.

A number of such devices are depicted in FIGS. 6-10. FIG. 6 depicts a series of tissue markers for use inside a human or animal body. Markers 60 may be laser-processed as described above with a series of small depressions or voids 61. In these embodiments, the marks have been placed at the corners to aid surgeons or other medical personnel in visualizing their shape and location. The tissue markers are preferable made from stainless steel or other material that is easily detected by a number of imaging techniques. FIG. 7 is an embodiment of the small laser-made voids or depressions in a cannula 70.

Voids or marks are preferably made near the tip 71 of cannula 70. In this embodiment, a first series of marks 72 nearer tip 71 are smaller and located more closely together, while a second series 73 are located a little farther from the tip. Marks in the second series 73 are distinct from those in the first series, the second series marks being larger and less closely spaced, and thus different under ultrasound or MRI from the first series. Thus, the first series of marks are of a different size and have a different distribution from the second series of marks.

FIG. 8 depicts a catheter 80 with a series 81 of small marks near the tip of the catheter. Catheters are typically made of plastic, such as polyethylene or polypropylene, or nylon. They may also be made of metal, such as stainless steel or other metal more suitable for detection under ultrasound or magnetic resonance imaging. Catheter 80 may be useful for opacifying the biliary or pancreatic duct during an endoscopic retrograde cholangiopancreatography procedure (ERCP). There are three bands 81, 82, 83 of echogenic marks placed near the distal end of the catheter. The bands may be spaced as desired, such as at 1 cm intervals.

FIG. 9 depicts a biopsy forceps 90 marked with two bands 92, 93 of small depressions on the jaws of the distal end. The marks make it easier for the surgeon or medical professional to guide the jaws when taking a biopsy sample. It should be noted that many of the diagnostic or therapeutic devices discussed with respect to echogenic marking are also meant to be used with an endoscope or other visualization tool. While the devices may be meant for visualization, there are many reasons why a surgeon may desire an independent method for determining exactly where the device is. For instance, the operating field may be obscured with blood or other fluid that makes visualization difficult. The surgeon may be better able to gauge the situation by seeing an ultrasound image, a fluoroscopic image, or a magnetic resonance image. This may also be the case when performing a percutaneous nephrolithotomy procedure, removing kidney stones with the extractor of FIG. 10. Extractor 100 includes a rigid cannula 101 with a distal tip 102 for deploying a basket 105 to remove kidney stones or calculi from a patient. Cannula 101 is preferably stainless steel or other metal that can be easily seen with several imaging techniques. The extractor is operated by squeezing handle 161, moving control rod 114 forward or backward, and deploying basket 105 from cannula 101. Distal tip 102 includes two bands 103, 104 of marks that allow easier visualization with ultrasonic techniques.

While many medical products are made from metal, such as guide wires and surgical needles, many other products may be made from elastomers and plastics, such as ABS, silicone, acrylic, polycarbonate, and nylon. These materials may be machined using lasers with the appropriate amount of energy to ablate material without burning or melting the material. Accordingly, embodiments of the invention are not limited to metallic medical devices, but may include medical devices made from elastomers and plastics, and any material which a laser is able to ablate and to from echogenic surfaces upon. This also includes composites or combinations of materials that may be ablated, such as a steel/plastic composite, or a steel/rubber composite.

It is therefore intended that the foregoing detailed description be regarded as illustrative rather than limiting, and that it be understood that it is the following claims, including all equivalents, that are intended to define the spirit and scope of this invention.

What is claimed is:

1. A medical device, comprising:
    a medical device with an external surface;
    a first plurality of small depressions on a portion of the external surface of the medical device, wherein each of the first plurality of small depressions has a first angle relative to the external surface of the medical device in the locations of the first plurality of depressions; and
    a second plurality of small depressions on the medical device, wherein each of the second plurality of small depressions has a second angle relative to the external surface of the medical device, such that the second angle differs from the first angle, wherein each of the first plurality of small depressions is symmetrical to the other small depressions of the first plurality and each of the second plurality of small depressions is unsymmetrical to both the other small depressions of the second plurality and the small depressions of the first plurality.

2. A medical device according to claim 1, wherein the medical device is selected from the group consisting of a guide wire, a needle, a stent, a dilator, an introducer, a lead, a cannula, a biopsy forceps, a biopsy needle, a tissue marker, a catheter, an angiography device, an angioplasty device, and a pump.

3. A medical device according to claim 1, wherein a majority of the first plurality of small depressions have a maximum dimension of from about 2 to about 100 micrometers.

4. A medical device according to claim 1, wherein a material for the external surface is selected from the group consisting of stainless steel alloy, an Inconel alloy, a Biodur alloy, a titanium alloy, a niobium alloy, a tantalum alloy, a molybdenum alloy, and MP35N.

5. A medical device according to claim 1, wherein the medical device has a longitudinal axis and the first plurality of small depressions are in a first orientation relative to the longitudinal axis and the second plurality of small depressions are in a second orientation relative to the longitudinal axis.

6. A medical device, comprising:
    a medical device with an external surface;
    a first plurality of small surfaces on a portion of the external surface of the medical device in a first orientation relative to the medical device and located at a plurality of depths;
    a second plurality of small surfaces on the medical device in a second orientation relative to the medical device, such that the orientation of the second plurality differs from the orientation of the first plurality, and such that the first orientation is not perpendicular to the second orientation.

7. A medical device according to claim 6, wherein the first plurality of small surfaces comprises a plurality of shapes.

8. A medical device according to claim 7, wherein the plurality of shapes render the surface visible with ultrasonic imaging equipment.

9. A medical device according to claim 6, wherein the first plurality of small surfaces is ablated in a plurality of sizes in which a first size is different from a second size by at least one of height, depth, width, diameter or circumference.

10. A method of making a medical device having an echogenic surface, the method comprising:
    ablating a first plurality of small depressions on at least a portion of an external surface of the medical device, wherein each of the first plurality of small depressions has a first orientation relative to the external surface of the medical device; and
    ablating a second plurality of small depressions on the medical device with a laser, wherein each of the second plurality of small depressions has a second orientation relative to the external surface of the medical device, such that the second orientation relative to the external surface of the medical device differs from the first orientation relative to the external surface of the medical device, wherein each of the first plurality of small depressions is symmetrical and each of the second plurality of small depressions is unsymmetrical; and cleaning the medical device.

11. A method of making a medical device according to claim 10, wherein the first plurality of small depressions has a distribution of depressions different from the second plurality.

12. A method of making a medical device according to claim 10, wherein the medical device has a longitudinal axis and the first plurality of small depressions are in a first orientation relative to the longitudinal axis and the second plurality of small depressions are in a second orientation relative to the longitudinal axis.

* * * * *

UNITED STATES PATENT AND TRADEMARK OFFICE
CERTIFICATE OF CORRECTION

PATENT NO. : 8,656,928 B2  Page 1 of 1
APPLICATION NO. : 11/665460
DATED : February 25, 2014
INVENTOR(S) : Carlson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1575 days.

Signed and Sealed this

Twenty-ninth Day of September, 2015

Michelle K. Lee
*Director of the United States Patent and Trademark Office*